United States Patent
Bordewick

(12) 
(10) Patent No.: US 6,431,172 B1
(45) Date of Patent: Aug. 13, 2002

(54) NASAL CANNULA WITH INFLATABLE PLENUM CHAMBER

(75) Inventor: Steve Bordewick, Shoreview, MN (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/692,172

(22) Filed: Oct. 20, 2000

(51) Int. Cl.⁷ .............................. A61M 15/08
(52) U.S. Cl. ................ 128/207.18; 128/206.11
(58) Field of Search ............ 128/200.24, 200.26, 128/204.11, 204.12, 206.11, 206.18, 206.21, 207.13, 207.18, 912, 203.22, 203.18, DIG. 26; 604/94.01; 606/199, 204.45

(56) References Cited

U.S. PATENT DOCUMENTS

| | | | |
|---|---|---|---|
| 2,763,263 A | * 9/1956 | Ellman | 128/198 |
| 3,513,844 A | * 5/1970 | Smith | 128/207.18 |
| 3,874,380 A | * 4/1975 | Baum | 128/200.14 |
| 3,902,486 A | * 9/1975 | Guichard | 128/203.22 |
| 4,367,735 A | * 1/1983 | Dali | 128/203.22 |
| 4,465,067 A | 8/1984 | Koch et al. | |
| 4,782,832 A | 11/1988 | Trimble et al. | |
| 4,915,105 A | 4/1990 | Lee | |
| 4,919,128 A | 4/1990 | Kopala et al. | |
| 5,042,478 A | 8/1991 | Kopala et al. | |
| 5,113,857 A | * 5/1992 | Dickerman et al. | 128/206.11 |
| 5,243,971 A | 9/1993 | Sullivan et al. | |
| 5,269,296 A | 12/1993 | Landis | |
| 5,477,852 A | * 12/1995 | Landis et al. | 128/204.18 |
| 5,682,881 A | 11/1997 | Winthrop et al. | |
| 5,687,715 A | 11/1997 | Landis et al. | |
| 5,752,510 A | * 5/1998 | Goldstein | 128/200.24 |
| 5,794,619 A | * 8/1998 | Edelman et al. | 128/200.24 |
| 6,354,293 B1 | * 3/2002 | Madison | 128/204.13 |

FOREIGN PATENT DOCUMENTS

WO    WO 90/01963    3/1990

* cited by examiner

*Primary Examiner*—Aaron J. Lewis
*Assistant Examiner*—Teena Mitchell
(74) *Attorney, Agent, or Firm*—Rothwell, Figg, Ernst & Manbeck

(57) ABSTRACT

A nasal cannula for delivering a breathing gas includes a rigid support adapted for placement at least partly beneath the nose of a user, an inflatable plenum chamber mounted on the rigid support, and a pair of nares elements mounted on the inflatable plenum chamber for insertion into the nostrils of the user. The inflatable plenum chamber includes a flexible membrane mounted on the rigid support. The flexible membrane can be preformed to define laterally spaced humps for mounting individual nares element and can further be pleated. Alternatively, a pair of inflatable plenum chambers can be separately mounted on the rigid support.

19 Claims, 3 Drawing Sheets

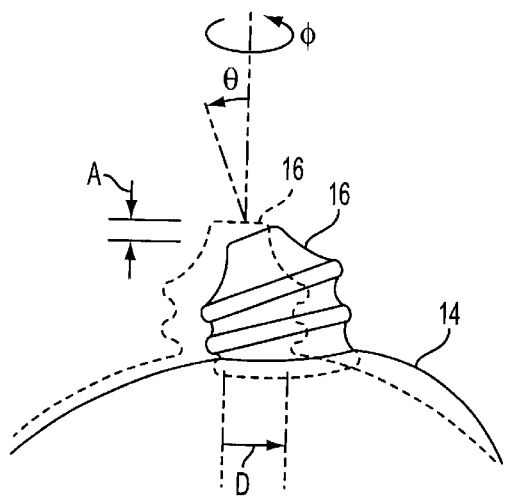
FIG. 4
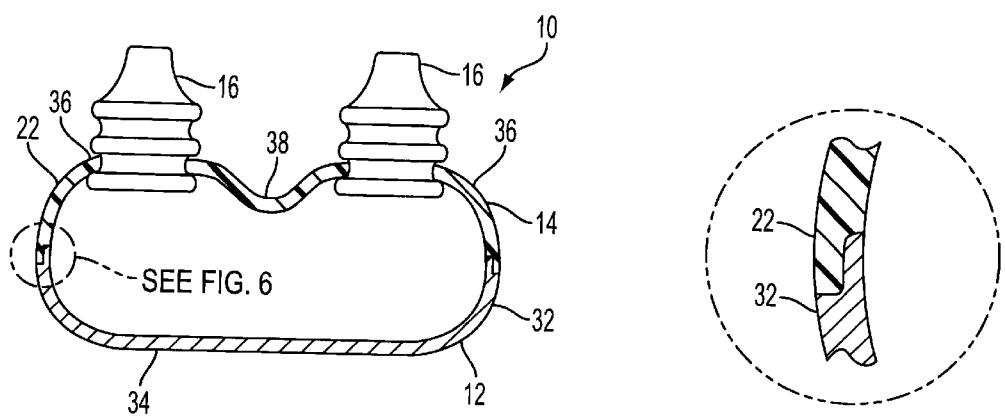
FIG. 5
FIG. 6
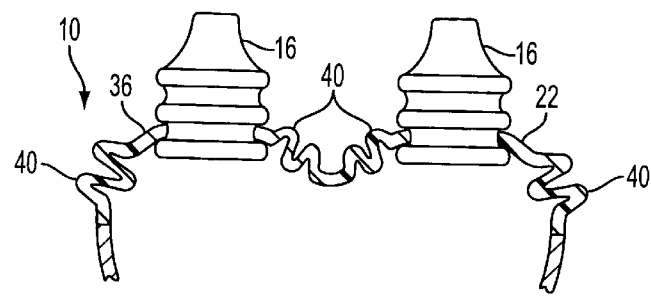
FIG. 7

NASAL CANNULA WITH INFLATABLE PLENUM CHAMBER

BACKGROUND OF THE INVENTION

1. Field of the Invention

The present invention relates generally to the field of respiratory therapy and, more particularly, to an apparatus and method for delivering a breathing gas to a patient.

2. Description of the Background Art

Continuous positive airway pressure (CPAP) therapy has been shown to be an effective treatment for obstructive sleep apnea, a condition in which the patient's airway passage is repeatedly blocked during a period of sleep resulting in interruption of the flow of air to the patient's lungs and causing the patient to awaken. CPAP therapy involves delivering a breathing gas at a constant gas pressure through the nasal passages to prevent negative pressure conditions within the upper air passageway which can lead to obstruction, thereby allowing continuous air flow through the upper air passageway. The gas is typically administered by placing a mask over the nose of the patient by means of a strap or harness or other headgear and providing a source of positive low pressure air connected to the mask.

Conventional nasal masks, exemplified by U.S. Pat. No. 4,655,213 to Rapoport et al., include a shell that contacts the face of the patient around the nose to form a seal. This type of mask is sometimes considered uncomfortable because of the contact pressure needed to obtain an adequate seal, and are often noisy due to air leaks. In many cases, use of a conventional mask represents a formidable obstacle to patient acceptance of CPAP therapy.

An alternative approach which has gained widespread acceptance, exemplified by U.S. Pat. No. 4,782,832 to Trimble et al., involves use of a nasal cannula having a pair of nares elements or inserts configured for insertion into the respective nostrils of a patient. The nares elements are mounted on a rigid plenum chamber extending from a gas inlet tube connected with a source of breathing gas and include passages formed therethrough in communication with openings in the plenum chamber. The outer wall of each nares element is generally frustoconically shaped so as to sealingly engage the nares-defining surface of the nose. Adjustability of the nares elements is provided by rotatably mounting the elements to the plenum chamber and mounting the elements in slots permitting selective lateral positioning of the elements with respect to each other. The nares elements can be provided with flexible corrugated sections to achieve greater degrees of flexibility and adjustability. The nares elements are also formed of a relatively soft, deformable, shape-retaining synthetic resin material permitting manual deformation and alteration of the effective shape and position of the elements.

A variation of the aforementioned nasal cannula, disclosed in U.S. Pat. No. 5,269,296 to Landis, includes nares elements with inflatable cuffs that engage the interior walls of the nose defining the nares in order to hold the cannula in place within the nares. The cuffs can be inflated by means of apertures formed in the side walls of the nares elements or, alternatively, by tubes delivering gas from a separate source of gas. The nasal cannula is held in place by an inflatable harness composed of hoses made of soft inflatable plastic which inflate upon application of air pressure to the hoses. While such an inflatable harness is potentially softer than a conventional harness, the increased bulk associated therewith can contribute to patient discomfort and the lack of rigidity can make it difficult to properly position and maintain the device in a desired position without frequent readjustment.

While the aforementioned nasal cannulae are an improvement over prior nasal masks, there continues to be a need for an improved nasal cannula that offers greater adjustability and comfort for the patient without added complexity.

SUMMARY OF THE INVENTION

Accordingly, it is a primary object of the present invention to provide a nasal cannula which overcomes the disadvantages of prior nasal masks and cannulae.

A first aspect of the present invention is generally characterized in a nasal cannula for delivering a breathing gas including a rigid support adapted for placement at least partly beneath the nose of a user, an inflatable plenum chamber mounted on the rigid support, and a pair of nares elements mounted on the inflatable plenum chamber for insertion into the nostrils of the user. The inflatable plenum chamber preferably includes at least one flexible membrane mounted on the rigid support. The flexible membrane can be preformed to define laterally spaced humps for mounting individual nares element and can further be pleated.

The nares elements can be mounted on a single inflatable plenum chamber or on separate inflatable plenum chambers. The nares elements can further be provided separately and attached to the inflatable plenum chamber or formed integrally as part of the plenum chamber. The inflatable plenum chamber can be fixed to the rigid support or detachably connected to the rigid support.

Another aspect of the present invention is generally characterized in a method of delivering a breathing gas using a nasal cannula including at least one inflatable plenum chamber mounted on a rigid support and a pair of nares elements mounted on the at least one inflatable plenum chamber. The method includes the steps of securing the nasal cannula to the head of the user, positioning the nasal cannula such that the nares elements are disposed within the nostrils of the user and the at least one inflatable plenum chamber is disposed between the nares elements and the rigid support, and delivering a breathing gas to the user via the inflatable plenum chamber and the nares elements.

The above and other features and advantages of the present invention will be further understood from the following description of the preferred embodiments thereof, taken in conjunction with the accompanying drawings in which like reference numerals are used to denote like parts.

BRIEF DESCRIPTION OF THE DRAWINGS

FIG. 4 shows how a nares element mounted on an inflatable plenum chamber can move with several degrees of freedom.

FIG. 5 shows a fragmentary front view, partly in section, of another embodiment of a nasal cannula according to the present invention.

FIG. 6 shows an enlarged fragmentary view, in section, of the interface between inflatable and rigid plenum portions of the nasal cannula of FIG. 5.

FIG. 7 shows a fragmentary front view, partly in section, of yet another embodiment of a nasal cannula according to the present invention.

DETAILED DESCRIPTION OF THE PREFERRED EMBODIMENTS

Figure 1:
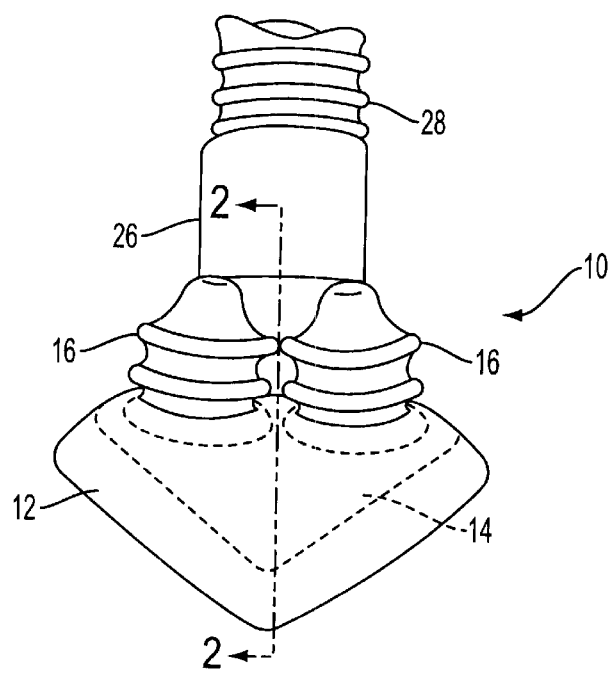
FIG. 1 shows a front view of a nasal cannula according to the present invention.
Figure 2:
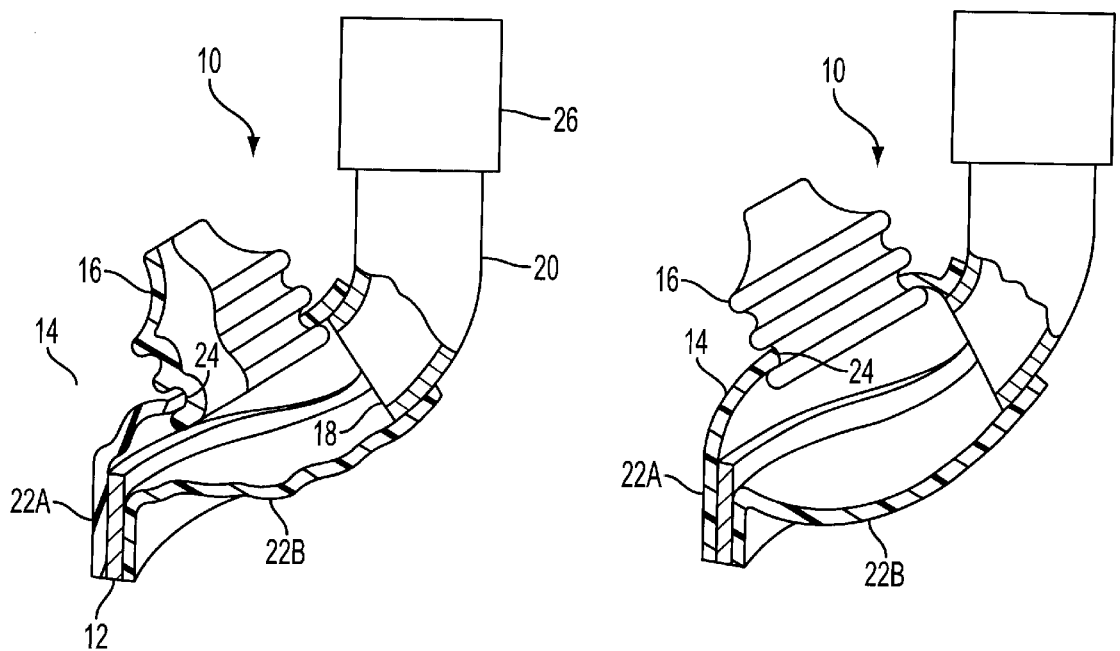
FIG. 2 shows a side view of the nasal cannula of FIG. 1, partly in section, with its plenum chamber deflated.

A nasal cannula 10 according to a first embodiment of the present invention is shown in FIGS. 1 and 2. FIG. 1 shows the nasal cannula looking distally, and FIG. 2 shows a side view of the nasal cannula with a partial section taken through line 2—2 in FIG. 1. Nasal cannula 10 includes a rigid support 12 for placement at least partly beneath the nose of a user, an inflatable plenum chamber 14 mounted on the support, and a pair of nares elements 16 mounted on the inflatable plenum chamber. Support 12 is shown as a generally diamond-shaped frame with a central opening. The support extends downwardly at an oblique angle from the proximal end 18 of an optional gas inlet tube 20. Inflatable plenum chamber 14 includes upper and lower flexible membranes 22A and 22B mounted on opposite sides of support frame to define a chamber therebetween in communication with a gas outlet at the proximal end of gas inlet tube 20. Upper membrane 22A is shown with a pair of laterally spaced gas outlets 24 formed therein for receiving nares elements 16.

The nares elements shown in FIGS. 1 and 2 are similar to those described in U.S. Pat. No. 4,782,832, the disclosure of which is incorporated herein by reference. These nares elements or inserts are generally frustoconical and mounted on a bellows 20 type corrugated section, with a central air passageway formed therethrough to permit gas flow from plenum chamber 14 into the nose. Elements 16 are preferably formed of a soft synthetic resin material, such as silicone, so as to allow axial and radial adjustment of the inserts to accommodate variations in the nasal passages of different wearers. While a particular type of nares element is shown and described, it will be appreciated that any type of soft, semi-soft, or hard nares element capable of forming a seal with a nasal passage can be used.

The optional gas inlet tube 20 is shown in FIGS. 1 and 2 with a fitting 26 at a distal end for receiving a gas hose 28 of the type commonly used to convey a breathing gas from a ventilator or respirator. Gas inlet tube 20 and support 12 can be formed of any medically acceptable rigid material but are preferably formed of rigid polycarbonate or PVC. The term "rigid" is used in a broad sense to mean subtantially non-deformable and non-inflatable under normal operating loads and pressures. If the gas inlet tube and the support are formed of the same material, it is possible to form them as an integral one-piece unit. The inflatable plenum chamber in general, and flexible membranes in particular, can be formed of any medically acceptable flexible material capable of being inflated by normal breathing gas pressures (e.g., about 3 to 35 cm $H_2O$) but are preferably formed of an elastomeric material such as silicone. In the case of the embodiment shown in FIGS. 1 and 2, marginal portions of the inflatable plenum chamber membranes 22A and 22B can be affixed to support 12 and inlet tube 20 using adhesives, co-molding, thermal welding, mechanical attachment or any other suitable techniques. Alternatively, a single membrane having a sock-like configuration can be slipped over the support and can be permanently or detachably affixed to the support and/or the tube instead of using two membranes.

In use, nasal cannula 10 is secured to the head of a patient such that nares elements 16 are inserted into the patient's nostrils and inflatable plenum 14 is disposed underneath the patient's nose between the nares elements and support 12. Support 12 extends distally from beneath the patient's nose to gas inlet tube 20 which extends upwardly to receive a gas supply hose 28 draped over the top of the patient's head. Standard straps and harnesses that extend around the head of the patient from the rigid portions of the nasal cannula are preferably used in securing the nasal cannula and hose to the patient; however, the mask can be attached to the wearer using any suitable headgear including, by way of example, anchors biased against the wearer's head as described in U.S. patent application Ser. No. 09/276,799, filed on Mar. 26, 1999, the disclosure of which is incorporated herein by reference.

Hose 28 connects the nasal cannula to a ventilator or respirator that generates a flow of breathing gas. Gas flowing from the generator is conveyed by hose 28 into gas inlet tube 20 which directs the gas into inflatable plenum chamber 14.

As shown in FIG. 2, inflatable plenum chamber 14 is flaccid when not pressurized by a breathing gas. In the uninflated or flaccid state, flexible membranes 22A and 22B are slack and are not effective in transmitting forces between nares elements 16 and rigid support 12. Nares elements 16 are thus loosely positioned in the user's nostrils without much force. Nevertheless, rigid support 12 provides sufficient structural support to maintain the nominal position of nares elements 16 relative to other parts of the nasal cannula so that initial alignment of the nares elements with the patient's nostrils can be accomplished.

Figure 3:
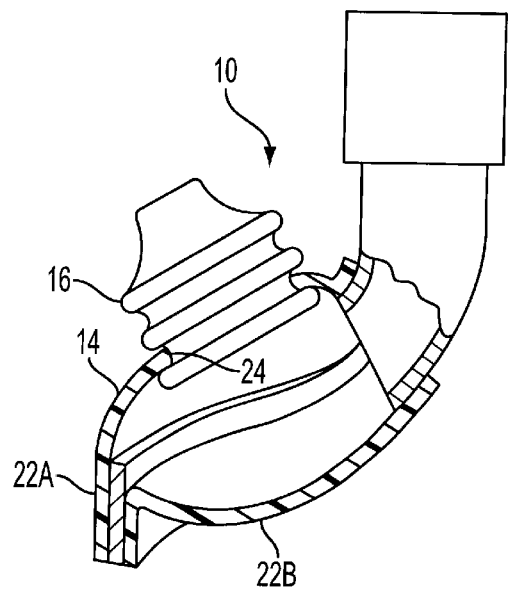
FIG. 3 shows a side view of the nasal cannula of FIG. 1, partly in section, with its plenum chamber inflated.

When pressurized by a breathing gas, plenum chamber 14 is inflated as shown in FIG. 3. In the inflated state, internal gas pressure within chamber 14 takes up the slack in membranes 22A and 22B, which expand outwardly to gently apply an inward retention force to nares elements 16. The use of internal gas pressure to regulate the amount of force applied to the nares elements is a major departure from prior art cannulae which rely on relatively non-compliant members such as straps to retain the nares elements in place within the nose.

From plenum chamber 14, the breathing gas flows into the nares elements 16 via outlets 24 in the chamber. The nares elements then direct the breathing gas into the patient's nostrils. To ensure a leak-free fit, the nares elements are preferably snugly positioned within the patient's nostrils. In the past, patients have experienced some discomfort from snugly fitted nares elements because of their tendency to transmit physical shocks and jolts to the sensitive nasal passages of the patient when fully compressed. In the present invention, however, the inflated plenum chamber offers additional compliance so that most shocks and jolts which would otherwise be transmitted to the patient are absorbed. It will also be appreciated that the added compliance of the inflatable plenum chamber provides additional degrees of freedom for movement of the nares elements while at the same time increasing the range of movement in all directions. This results in improved adjustability of the nares elements, allowing the nasal cannula to accommodate large physical differences between patients. FIG. 4 shows how a nares element 16 mounted on an inflatable plenum chamber 14 can move with five or more degrees of freedom. For example, the nares element can move axially along its long axis as indicated at "A", or translate laterally in orthogonal directions perpendicular to its long axis as indicated at "D", or tilt relative to its long axis as indicated at "θ", or rotate about its long axis as indicated at "ψ", or some combination of the movements in the foregoing directions.

Another embodiment of a nasal cannula 10 according to the present invention is shown partly in section in FIGS. 5 and 6. The nasal cannula in this embodiment is similar to the nasal cannula described in conjunction with FIGS. 1 and 2, but with a solid support 12 defining a lower portion of the inflatable plenum chamber 14 and a flexible membrane 22 preformed to increase isolation of the nares elements from one another in the inflated state. Support 12 includes sidewalls 32 that extend upwardly from a bottom wall 34 to define a compartment with an open top. A flexible membrane 22 extends across the open top of the compartment to define an inflatable plenum chamber 14 in conjunction therewith. As best seen in FIG. 6, flexible membrane 22 is molded into grooves formed in sidewalls 32 of the support to present a substantially flush outer surface without protruding edges that could irritate a user. It will be appreciated, however, that edges of the flexible membrane could be connected to the sidewalls using an interior or exterior lap joint. As best seen in FIG. 5, flexible membrane 22 is preformed to define laterally spaced humps 36 separated by a recess 38 in the inflated state. Nares elements 16 are mounted on the elevated regions or humps 36 to permit a greater degree of independent movement. Alternatively, the flexible membrane can form a single hump as shown in FIG. 1. As a further alternative, the solid support can be replaced by a support in the form of a frame with the inflatable plenum being formed by a pair of membranes on opposite sides of the frame, at least one of the membranes being preformed to define plural humps in an inflated state.

FIG. 7 shows a fragmentary view of still another embodiment of a nasal cannula 10 according to the present invention having a modified flexible membrane 22. Nasal cannula 10 in FIG. 7 is similar to the nasal cannula described in conjunction with FIG. 5, however, flexible membrane 22 is formed with pleats or folds 40 about the circumference of each hump 36 allowing a greater range of movement of the nares elements 16 in the lateral direction.

Figure 8:
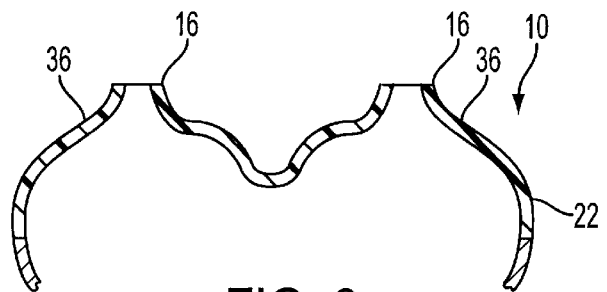
FIG. 8 shows a fragmentary front view, in section, of still another embodiment of a nasal cannula according to the present invention.

FIG. 8 shows a fragmentary view of an additional embodiment of a nasal cannula 10 according to the present invention having a modified flexible membrane 22. Flexible membrane 22 is similar to the flexible membrane described in conjunction with FIG. 5 but defines integral nares elements 16 on each hump 36. The nares elements 16 have smoothly sloping walls but could be formed with pleats or folds if desired.

Figure 9:
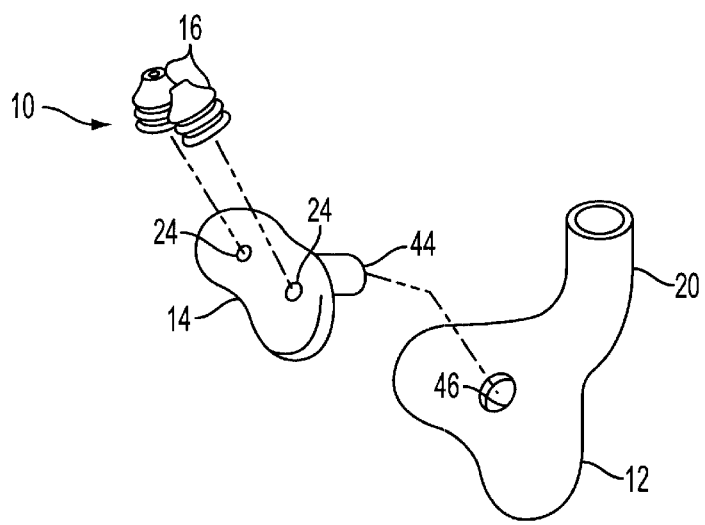
FIG. 9 shows an exploded view of a further embodiment of a nasal cannula according to the present invention.

A further embodiment of a nasal cannula 10 according to the present invention is shown in FIG. 9. In this embodiment, support 12 is a rigid hollow member defining a rigid plenum chamber in fluid communication with gas inlet tube 20 and the inflatable plenum chamber 14 is mounted on the rigid plenum chamber. Inflatable plenum chamber 14 is a bag formed of a flexible membrane with a pair of laterally spaced gas outlets 24 on a top surface thereof for receiving nares elements 16 and a tubular gas inlet 44 on a bottom surface thereof for communicating with an opening 46 in the support.

Figure 10:
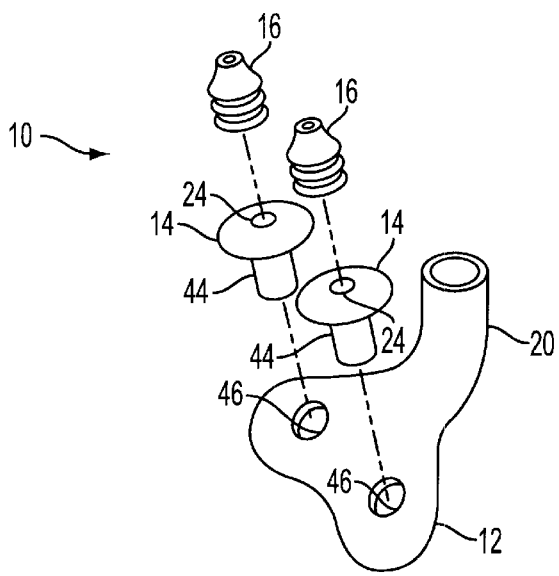
FIG. 10 shows an exploded view of an additional embodiment of a nasal cannula according to the present invention.

Still another embodiment of a nasal cannula 10 according to the present invention is shown in FIG. 10. Nasal cannula 10 is similar to the nasal cannula described in conjunction with FIG. 9 but includes a pair of inflatable plenum chambers 14 mounted in lateral relation to one another on a rigid plenum chamber defined by a hollow rigid support 12. Support 12 includes a pair of gas outlet openings 46, and each of the inflatable plenum chambers 14 includes a tubular gas inlet 44 configured to communicate with a gas outlet 46 in the support. Inflatable plenum chambers 14 each have a gas outlet 24 configured to receive one of the nares elements 16.

The nasal cannulae 10 shown in FIGS. 9 and 10 are advantageous in that they facilitate easy removal of the inflatable plenum chambers from the supports to permit sterilization and reuse of the supports, and/or replacement of one type of inflatable plenum chamber with another type of inflatable plenum chamber. While separate nares elements are shown, it will be appreciated that the nares elements can be formed as integral parts of the plenum chamber as shown in FIG. 8.

The nasal cannula of the present invention can be used to deliver one or more gases to a patient in connection with any type of respiratory therapy, but is particularly useful in administering CPAP and BiPAP therapy to patients suffering from obstructive sleep apnea.

While the invention has been described in detail above, the invention is not intended to be limited to the specific embodiments as described. It is evident that those skilled in the art may now make numerous uses and modifications of and departures from the specific embodiments described herein without departing from the inventive concepts. For example, a vent aperture can be formed in any portion of the nasal cannula to expel the carbon-dioxide laden gases exhaled by the patient between breaths. Any conventional vent aperture can be used including, by way of example, the vent configuration described in the U.S. Pat. No. 5,065,756 to Rapoport, the disclosure of which is incorporated herein by reference. By way of further example, the vertical gas inlet tube can be replaced by a horizontal tube that extends laterally across the face, or a tube oriented perpendicular to the face. When a single inflatable plenum chamber is provided, independent movement of the nares elements can be enhanced by structures, such as walls or baffles, disposed within the inflatable plenum chamber. When a pair of inflatable plenum chambers are provided, the inflatable chambers can be mounted on a single support or individually mounted on a pair of supports.

What is claimed is:

1. A nasal cannula for delivering a breathing gas to a user, said nasal cannula comprising
   a rigid support adapted for placement at least partly beneath the nose of the user;
   an inflatable plenum chamber mounted on said rigid support, said inflatable plenum chamber having at least one gas inlet and at least one gas outlet; and
   at least one nares element mounted on said inflatable plenum chamber, said nares element having a gas flow passage therethrough in communication with said gas outlet.

2. A nasal cannula as set forth in claim 1, further comprising a rigid gas inlet tube having a gas outlet in communication with said at least one gas inlet of said inflatable plenum chamber.

3. A nasal cannula as set forth in claim 2, wherein said gas inlet tube has proximal and distal ends, and wherein said rigid support extends from said proximal end of said gas inlet tube.

4. A nasal cannula as set forth in claim 2, wherein said gas inlet tube and said support are formed as an integral one-piece unit.

5. A nasal cannula as set forth in claim 1, wherein said rigid support is a frame having at least one opening formed therein.

6. A nasal cannula as set forth in claim 5, wherein said inflatable plenum chamber includes a pair of flexible membranes mounted on opposite sides of said frame to define a plenum chamber therebetween.

7. A nasal cannula as set forth in claim 1, wherein said inflatable plenum chamber includes a flexible membrane, and wherein said rigid support and said flexible membrane cooperate to define said inflatable plenum chamber.

8. A nasal cannula as set forth in claim 1, wherein said rigid support is solid and said inflatable plenum chamber includes a membrane mounted on said rigid support to define a plenum chamber therebetween.

9. A nasal cannula as set forth in claim 1, wherein said at least one nares element is formed by said membrane.

10. A nasal cannula as set forth in claim 1, wherein said inflatable plenum chamber includes a pleated membrane.

11. A nasal cannula as set forth in claim 1, wherein said inflatable plenum chamber is removably mounted on said rigid support for disassembly from said cannula.

12. A nasal cannula as set forth in claim 1, wherein said inflatable plenum chamber includes a flexible membrane preformed to define a pair of humps in an inflated state.

13. A nasal cannula as set forth in claim 12, wherein a pair of nares elements are mounted on said humps.

14. A nasal cannula as set forth in claim 12, wherein said flexible member is pleated circumferentially around said humps.

15. A nasal cannula as set forth in claim 1, wherein said inflatable plenum chamber is a first inflatable plenum chamber with an inlet and an outlet, and further comprising a second inflatable plenum chamber with an inlet and an outlet mounted on said rigid support, wherein one of said nares elements is mounted on said first inflatable plenum chamber and the other of said nares elements is mounted on said second inflatable plenum chamber.

16. A nasal cannula as set forth in claim 1, wherein said at least one nares element includes a corrugated portion providing compliancy.

17. A method of delivering a breathing gas to a user, said method comprising the steps of securing a nasal cannula to the head of the user, the nasal cannula including at least one inflatable plenum chamber mounted on a rigid support and a pair of nares elements mounted on the at least one inflatable plenum chamber;

positioning the nasal cannula such that the nares elements are disposed within the nostrils of the user and the at least one inflatable plenum chamber is disposed between the nares elements and the rigid support; and delivering a breathing gas to the user via the inflatable plenum chamber and the nares elements.

18. A method as set forth in claim 17, wherein the rigid support is attached to a gas inlet tube, and further comprising the steps of attaching the at least one inflatable plenum chamber to one end of the gas inlet tube and attaching the opposite end of the gas inlet tube to a source of breathing gas.

19. A method as set forth in claim 17, and further comprising the step of detaching the at least one inflatable plenum chamber from the rigid support.

* * * * *